(12) United States Patent
Baierl et al.

(10) Patent No.: US 7,921,892 B2
(45) Date of Patent: Apr. 12, 2011

(54) CORRUGATING MACHINE

(75) Inventors: Klaus Baierl, Grafenwohr (DE); Norbert Stadele, Parkstein (DE)

(73) Assignee: BHS Corrugated Maschinen-und Anlagenbau GmbH, Weiherhammer (DE)

( * ) Notice: Subject to any disclaimer, the term of this patent is extended or adjusted under 35 U.S.C. 154(b) by 1225 days.

(21) Appl. No.: 11/422,344

(22) Filed: Jun. 6, 2006

(65) Prior Publication Data
US 2006/0278342 A1 Dec. 14, 2006

(30) Foreign Application Priority Data

Jun. 8, 2005 (DE) .......................... 10 2005 026 532

(51) Int. Cl.
*B32B 37/00* (2006.01)
(52) U.S. Cl. .......... 156/378; 156/64; 156/202; 156/205; 156/206; 156/350; 156/351; 156/379
(58) Field of Classification Search .................... 156/64, 156/202, 205, 206, 350, 351, 378, 379
See application file for complete search history.

(56) References Cited

U.S. PATENT DOCUMENTS

| | | | | |
|---|---|---|---|---|
| 4,856,334 A * | 8/1989 | Shearer et al. | ................... | 73/588 |
| 5,834,877 A * | 11/1998 | Buisker et al. | ................ | 310/322 |
| 6,840,108 B2 * | 1/2005 | Stauffer | .......................... | 73/630 |
| 7,275,438 B2 * | 10/2007 | Focke et al. | ...................... | 73/617 |
| 2004/0182504 A1 * | 9/2004 | Stadele et al. | ................. | 156/210 |

FOREIGN PATENT DOCUMENTS

| | | |
|---|---|---|
| DE | 86 32 116.1 | 7/1987 |
| DE | 3048710 C2 | 1/1992 |
| DE | 4305158 A1 | 8/1994 |
| DE | 19536007 A1 | 4/1997 |
| DE | 19754799 A1 | 6/1999 |
| DE | 19954754 A1 | 5/2001 |
| DE | 19955917 A1 | 5/2001 |
| DE | 10131833 A1 | 1/2003 |

(Continued)

OTHER PUBLICATIONS

Search Report for priority DE case from which this case claims priority.

(Continued)

*Primary Examiner* — Kat Wyrozebski
*Assistant Examiner* — Joshel Rivera
(74) *Attorney, Agent, or Firm* — James B. Conte; Husch Blackwell LLP

(57) ABSTRACT

The invention relates to a machine for the manufacture of a web of corrugated board which is conveyed in a working direction and comprises at least one smooth liner and at least one corrugated medium that has corrugation tips and corrugation troughs, the corrugated medium being applied by adhesion to the at least one liner at least in the vicinity of the corrugation troughs, wherein a quality assessment device for assessment of the quality of the adhesive bond between the at least one liner and the at least one corrugated medium is provided, which comprises at least one ultrasonic transmitter that is disposed on one side of the web of corrugated board and at least one ultrasonic receiver that is disposed on the opposite side of the web of corrugated board and is allocated to the at least one ultrasonic transmitter; and a control anti evaluation unit which, in a manner for data transmission, is connected to the at least one ultrasonic receiver for evaluation of the signal of the ultrasonic receiver.

8 Claims, 7 Drawing Sheets

FOREIGN PATENT DOCUMENTS

| | | |
|---|---|---|
| DE | 10318756 A1 | 4/2003 |
| DE | 20312388 U1 | 12/2003 |
| DE | 102004056743 A1 | 8/2005 |
| EP | 0687552 A2 | 12/1995 |
| GB | 2305675 | 4/1997 |
| GB | 2369186 | 5/2002 |
| WO | WO 2004033305 A1 * | 4/2004 |

OTHER PUBLICATIONS

EU Serach report for sister EU case EP 0601 0231.

* cited by examiner

CORRUGATING MACHINE

BACKGROUND OF THE INVENTION

1. Field of the Invention

The invention relates to a corrugating machine, comprising a device for quality assessment of the adhesive bond between the various webs of material.

2. Background Art

GB2 369 186 A describes an apparatus for continuously checking the quality of a web of corrugated board produced in a corrugating machine. To this end, tire moved web of corrugated board is provided with a mechanical vibration sensor which is set vibrating upon conveyance of the web of corrugated board. The kind of vibrations suggests the quality of the adhesive bond. Drawbacks reside in that the sensor is in permanent mechanical contact with the web of corrugated board, giving rise to wear on both parts. Moreover, the mechanical inertia of the sensor complicates the examination of the web of corrugated board at high conveying velocities of, for example, 400 m/min.

DE 199 55 917 A1 also teaches a corrugating machine with a quality assessment device. Optical distance sensors are provided on both sides of a web of single-faced corrugated board so that the precise course of the corrugated medium can be computed from the assessed data. To this end, enormous quantities of data must be processed. Column 3, line 31f, fundamentally mentions that, in lieu of the laser sensors used for distance measurement, corresponding ultrasonic sensors may be used for ultrasonic scanning of the corrugated medium. It is not said how this is handled in detail. In this case too, what is determined are the distances of the outside of the web of corrugated board from the sensors so that again great quantities of data will have to be processed.

SUMMARY OF THE INVENTION

It is an object of the invention to embody a corrugating machine in which as easily a possible to determine the quality of the adhesive bonding in a web of corrugated board.

This object is attained by the features of claim 1. The gist of the invention resides in that an ultrasonic transmitter is disposed on one side of the web of corrugated board and an ultrasonic receiver on the opposite side. The better the adhesive bond, the stronger the transmission of ultrasound through the web of corrugated board. If the adhesive bond is defective, the intensity of the ultrasound transmitted through the board will decrease strongly. The method can also be used for webs of corrugated board that are comprised of more than two webs of material.

Further advantageous embodiments of the invention will become apparent front the sub-claims.

Additional features and details of the invention will become apparent from the description of an exemplary embodiment, taken in conjunction with the drawing.

DESCRIPTION OF THE PREFERRED EMBODIMENT

Figure 1:
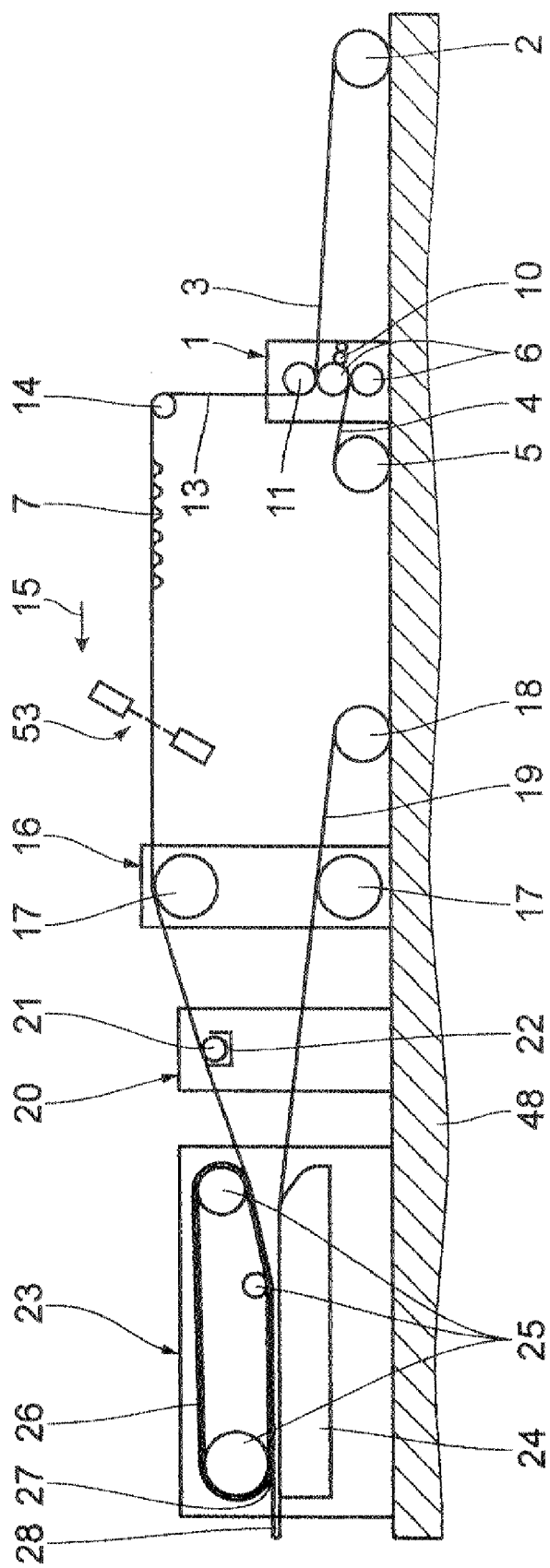
FIG. 1 is a view of a first part of a corrugating machine according to a first embodiment.

The following is a description of a first embodiment of the invention in conjunction with FIGS. 1 to 6. A corrugating machine as diagrammatically outlined in FIGS. 1 to 5 comprises a machine 1 for the manufacture of single-faced corrugated board. From a first unroll stand 2, a first web of material 3 is supplied to the machine 1. The webs of material are continuous webs of paper. The web of material 3 is a first liner for the corrugated board manufactured on the machine 1. The first web of material 3 and a second web of material 4, which is fed front a second unroll stand 5, are brought together in the machine 1. Being unrolled, the second web of material 4 passes between two adjacent corrugating rolls 6 for production of a corrugation in the machine 1. The second web of material 4, after passing through, constitutes a corrugated medium 7, which comprises a succession of corrugation tips 8 and corrugation troughs 9. Then adhesive is spread on the corrugated medium 7 in an adhesive applicator 10 and the medium 7 and the first web of material 3, a liner, are pressed and joined to each other in a nip between a flip roll 11 and one of the corrugating rolls 6 in the machine 1, an adhesive bond 12 originating. The originating web of single-faced corrugated board 13 made of the liner 3 and the corrugated medium 7 is delivered upwards and deflected by a defection roll 14 in a working direction 15. The machine 1 for the manufacture of webs of single-faced corrugated board is generally known, for example, from EP 0687 552 A (corresponding to U.S. Pat. No. 5,632,850), DE 195 36 007 A (corresponding to GB 2,305,675 A) of DE 43 05 158 A, which reference is made to for any details.

A pre-heater 16 is situated downstream of the machine 1 in the working direction 15. It comprises two heating rolls 17 which are disposed one on top of the other and which are heatable. Directed upstream of the pre-heater 16, provision is made for a second unroll stand 18 for a third web of material 19 which is unrolled therefrom and conveyed through the pre-heater 16 in the working direction 15. The web of single-faced corrugated board 13 and the third web of material 19 both partially envelop the heating rolls 17 and are led past them in the direction 15. Downstream of the pre-heater 16 in the direction 15, provision is made for an adhesive applicator unit 20 with an adhesive applicator roil 21 which partially dips into an adhesive bath 22. The corrugated medium 7 of the web of corrugated board 13 is in contact with the adhesive applicator roll 21.

A heater and nip pressure unit 23 is disposed downstream of the adhesive applicator unit 20, having a horizontal table 24 with heating plates that extends in the working direction 15. A driven, continuous nip pressure belt 26, which is deflected by three rolls 25, is provided above the table 24. A nip 27 is formed between the nip pressure belt 26 and the table 24, which the web of corrugated board 13 and the third web of material 19 are led through and where they are pressed together. A corresponding heater and nip pressure unit 23 is known from DE 199 54 754 A. A three-layer web of corrugated board 28 is formed in the heater and nip pressure unit 23.

Figure 2:
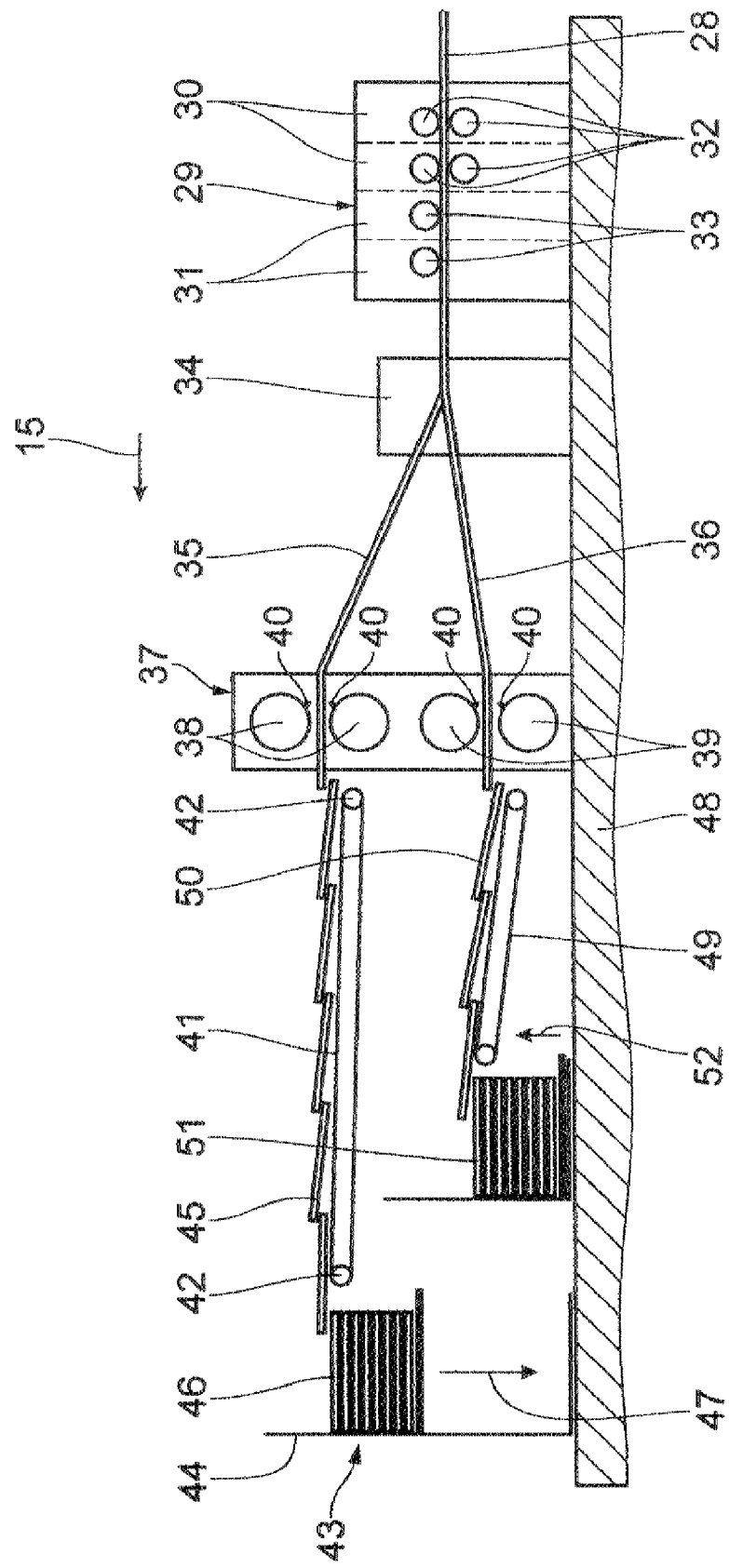
FIG. 2 is a view of a second par of a corrugating machine according to a first embodiment.

FIG. 2 shows a second part of the corrugating machine which is subsequent to the exit of the web of corrugated board 28 from the heater and nip pressure unit 23. What follows is a longitudinal cutter and scorer unit 29 composed of two successive scorer stations 30 as well as two successive longitudinal cutter stations 31. The score stations 30 comprise scoring tools 32 which are disposed one on top of the other in pairs and between which passes the web of corrugated board 28. Each longitudinal cutter station 31 comprises a rotarily drivable blade 33, the blades 33 being engageable with the web of corrugated board 28 for it to be severed longitudinally. The precise design of the longitudinal cutter and scorer unit 29 is known from DE 197 54 799 A (corresponding to U.S. Pat. No. 6,071,222) and DE 101 31 833 A, to which reference is made for details. Downstream of the longitudinal cutter and scorer unit 29 in the working direction, provision is made for a switch 34 where longitudinally cut, divisional webs 355 36 of the web of corrugated board 28 are separated from each other. The divisional webs 35, 36 are then supplied to a cross cutter 37. It comprises a top pair of cross cutter rolls 38 for the top divisional web 35 and a bottom pair of cross cutter rolls 39 for the bottom divisional web 36. The rolls of the pairs of rolls 38, 39 each have a blade 40 which extends radially outwards and is perpendicular to the working direction 15. The blades 40 of a pair of cross cutter rolls 38, 39 cooperate for crosswise cutting divisional webs 36. A top conveyor belt 41 is disposed downstream of the top pair of cross cutter rolls 38; it is deflected by rotarily drivable rolls 42. Downstream of the top convey, or belt 41, provision is made for a deposit 43 with a vertical stop 44 where sheets of corrugated board 45, cut from the divisional web 3 by the cross cutter 37, are piled on a stack 46. The deposit 43 is adjustable in height as roughly outlined by a directional arrow 47. In particular, the deposit 43, for further conveyance of the stack 46 can be lowered as far as to a machine bottom 48 which supports the corrugating machine. Another bottom conveyor belt 49 is disposed downstream of the bottom pair of cross cutter rolls 39, on another deposit 51 stacking sheets of corrugated board 50 which have been cut from the divisional web 36 by the cross cutter 37. For adaptation to the height of the stack 46, the bottom conveyor belt 49 can be lifted as outlined by a directional arrow 52.

Figure 3:
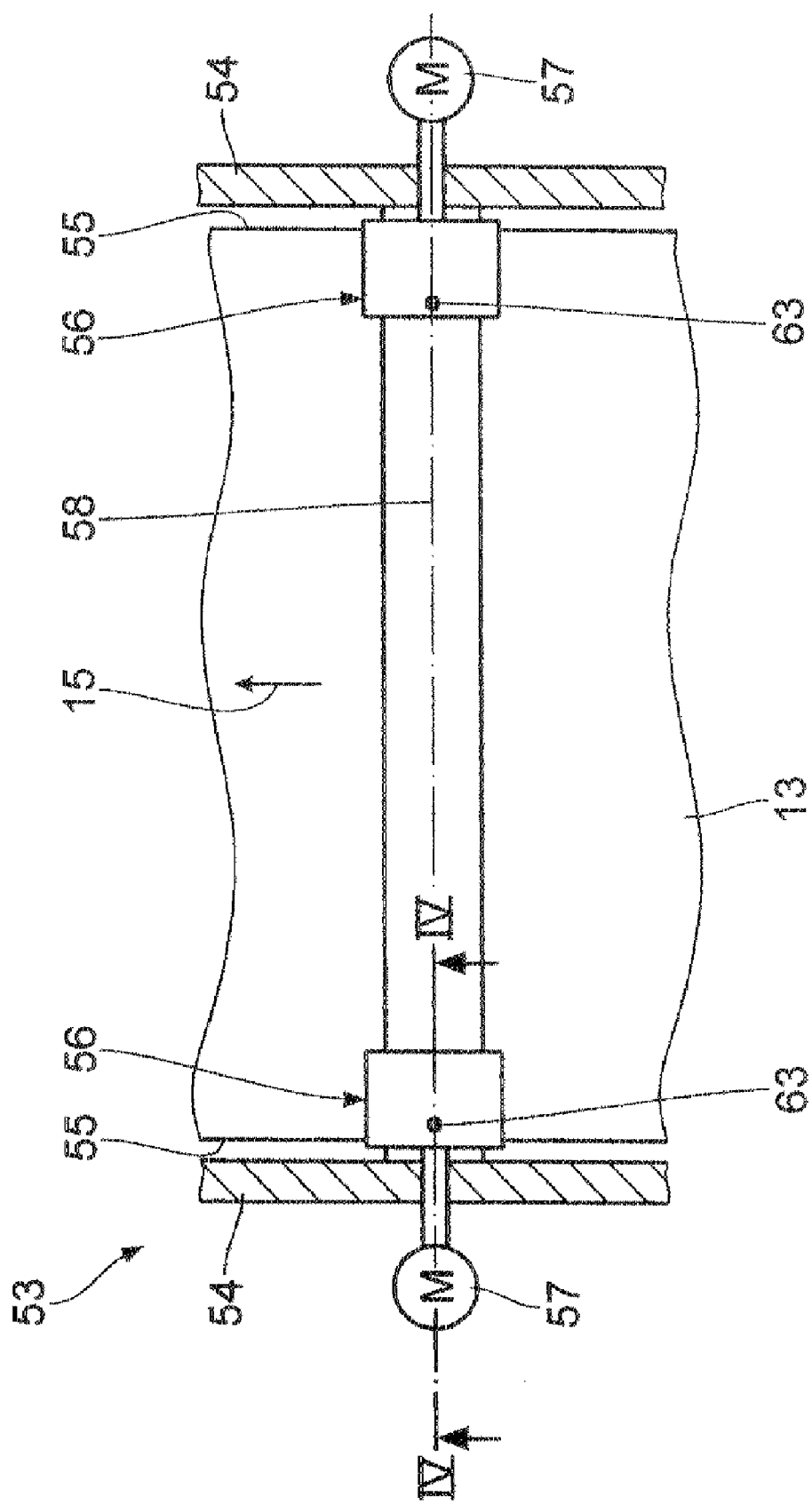
FIG. 3 is a plan view of a quality assessment device in a corrugating machine according to FIGS. 1 and 2.
Figure 4:
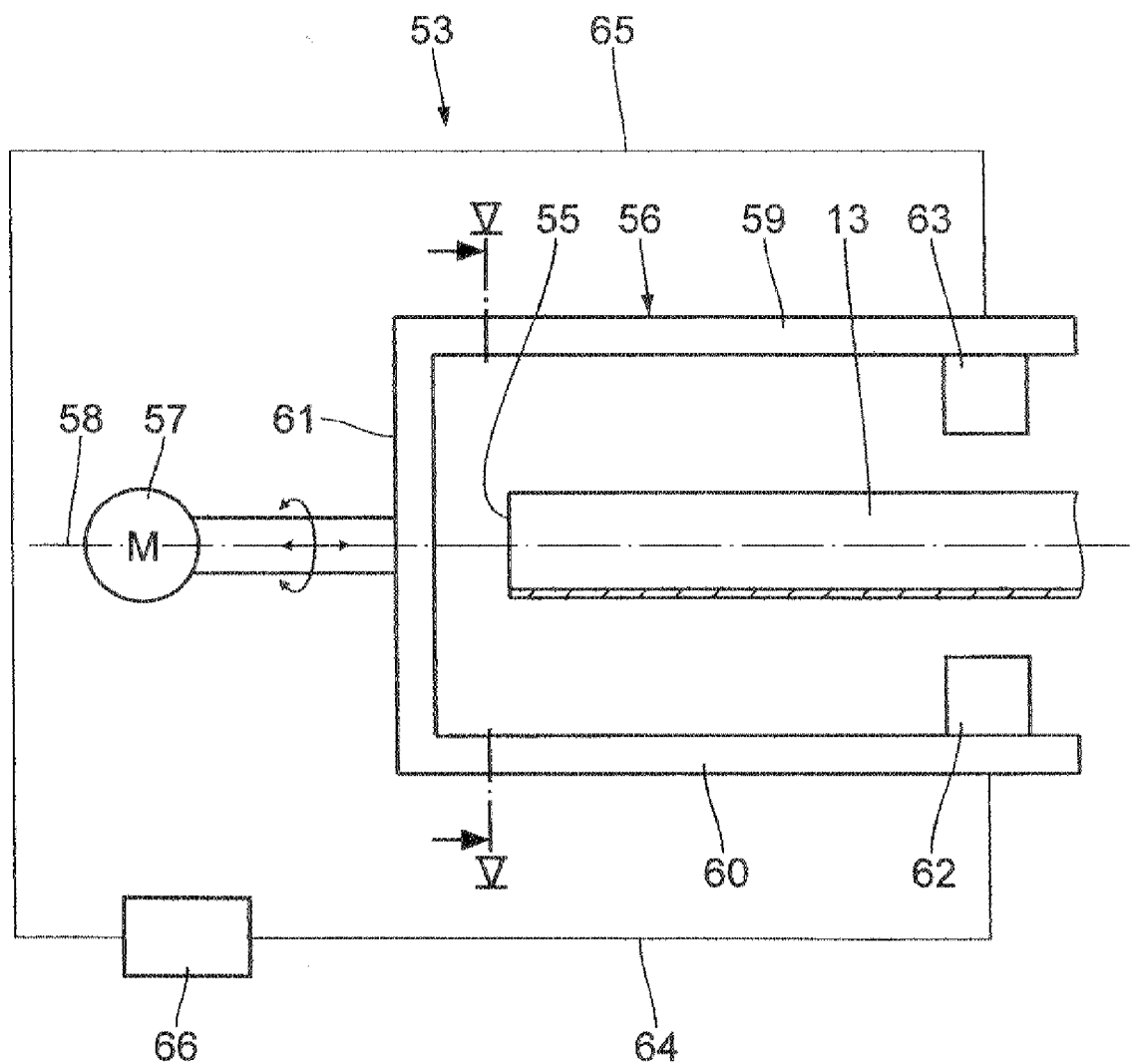
FIG. 4 is a sectional view on the line V-V of FIG. 3.
Figure 5:
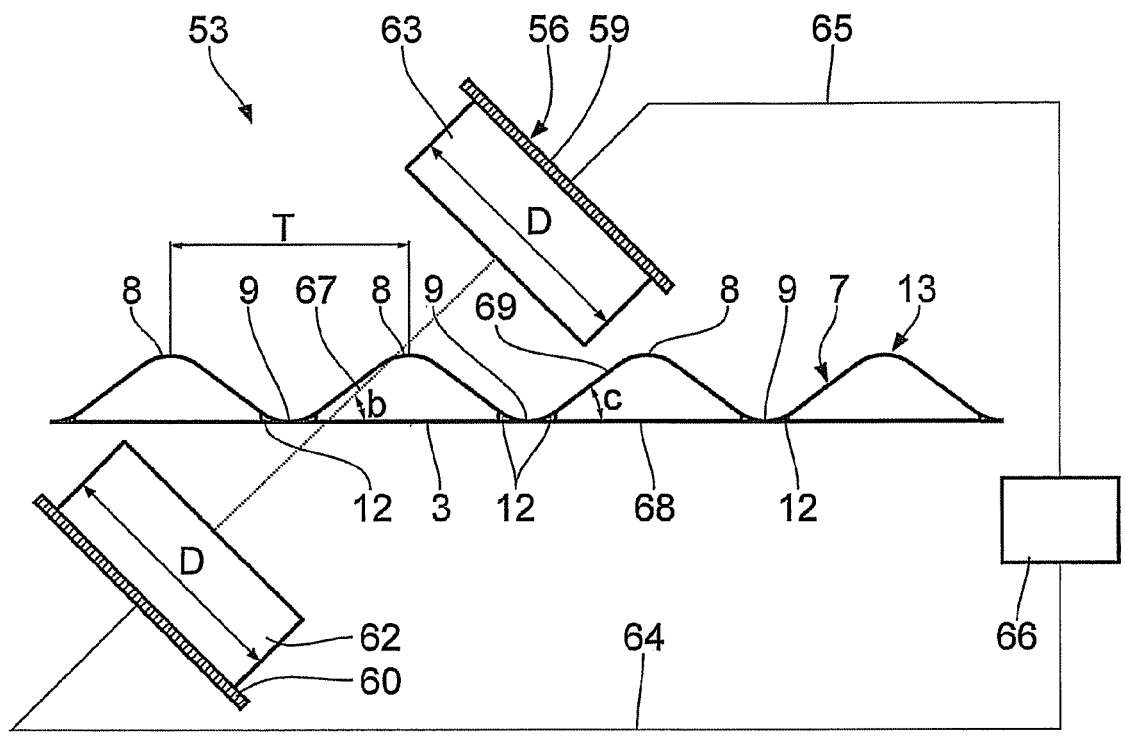
FIG. 5 is a sectional view on the line IV-IV of FIG. 3.

The corrugating machine comprises a quality assessment device 53 which is seen in detail in FIGS. 3 to 5. It assesses the quality of the adhesive bonds 12 in the web of single-faced corrugated board 13. In this regard tile device 53 is disposed, in the working direction 15, downstream of the machine 1 and upstream of the heater and nip pressure unit 23 where the third web of material 19 is applied. Placement between the machine 1 and the pre-heater 16 is preferred. The device 53 comprises props 54 which support themselves on the machine bottom 48 on both sides of the web of corrugated board 13. A support 56 is disposed and supported on each of the two props 54; it is U-shaped cross-sectionally and enclasps the margin 55 of the web of corrugated board 13. Outside the prop 54, provision is made for a drive mechanism 57 which allows pivoting about a pivoting axis 58. The pivoting axis 58 is located centrally on the web of corrugated board 13, extending vertically to the working direction 15. The drive mechanism 57 further enables the support 56 to be moved along the pivoting axis 58 so that the U-shaped support 56 can be slipped over the margin 55 even in case of smaller widths of the web of corrugated board 13. The support 56 has two legs 59, 60 which are parallel to each other and which are united by a joint base plate 61 that is perpendicular thereto, thus being formed as one piece therewith. An ultrasonic transmitter 62 is disposed on the inside of the leg 60. An associated ultrasonic receiver 63 is disposed on the opposite inside of the leg 59. The transmitter 62 and the receiver 63 have the same transversal position in relation to the web of corrugated board 13 i.e., they have the same vertical distance form the margin 55 of the web of corrugated board 13. The transmitter 62 is connected via a line 64, and the receiver 63 via a line 65, to a joint control and evaluation unit 66 in a manner for data transmission.

The transmitter 62 and the receiver 63 are located on a joint central longitudinal straight line 67. The second web of material 4 is situated on a plane 68 that defines it. The straight line 67 and the plane 68 make and angle b. The angle b is adjustable by the support 56 pivoting about the axis 58.

A flank 69 is located between every corrugating tip 8 and corrugation trough 9, together with the plane 68 making an angle c. The angle b is chosen such that, if possible, it corresponds to the angle c, which means that the ultrasound is transmitted as far as possible by the flank 69 of the corrugated medium 7 itself and not by the surrounding air. As for the angle b, $0° \leq b \leq 90°$, in particular $0° < b < 90°$, in particular $15° \leq b \leq 65°$, in particular $35° \leq b \leq 45°$, in particular $b \approx 40°$ applies fundamentally. Because of the pivotability of the support 56, the angle b can be adapted to the flank angle c for various types of corrugated board. The ultrasound transmitter 62 works for example at a frequency of approximately 200 kHz. The illustration of FIG. 5 is not trite to scale in as much as the web of corrugated board 13 is enlarged superproportionally. Fundamentally, the web of corrugated board 13 has a spacing T. The transmitter 62 and receiver 63 each have a diameter D. Preferably the diameter D must exceed the spacing T. Typical diameters D amount to 16 mm or 20 mm. The positions of the transmitter 62 and receiver 63 can also be interchanged. Moreover, it is possible to provide an arrangement that results from the transmitter 62 and receiver 63 being rotated counter-clockwise by an angle of 180°-2b about the intersection of the straight line 67 and the plane 68. In this way, the upstream position of the transmitter or receiver, respectively, is interchanged for a downstream position and vice versa. However, the angle b if the amount remains; it is then measured on the left of the axis 67 instead of on the right as seen in FIG. 5.

Figure 6:
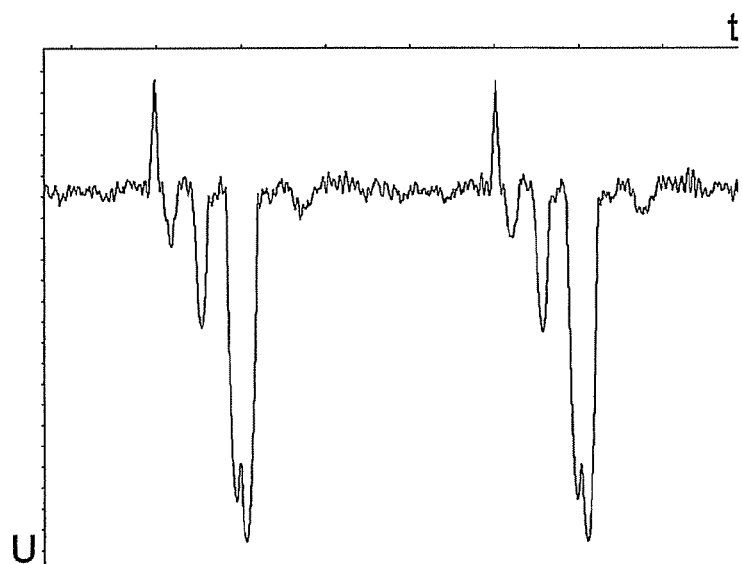
FIG. 6 is a potential-to-time diagram produced by the ultrasonic receiver in the vicinity of a faulty adhesive bond.

The mode of operation of the quality assessment device 53 will be described below, taken in conjunction with FIG. 6. Once the machine 1 has produced the web of single-faced corrugated board 13, the web is led through the device 3 at a known speed. The transveral positions of both supports 56 are set for enclasping, however not touching, both margins 55 of the web of corrugated board 13. The ultrasonic transmitter 62 constantly emits ultrasonic waves which are received by the associated ultrasonic receiver 63. Due to the fact that ultrasound is transmitted by far better by mass i.e., by paper, than by the air, a pulsatory signal originates in the case of perfect adhesive bonds 12, depending on whether the signal—as in FIG. 5—is being transmitted substantially by the flank 69 or shortly afterwards substantially by the ah. With the angle b=90°, the differences in signal intensity at the receiver 63 between a then passing corrugation tip 8 and a corrugation trough 9 would be very low, the ultrasound in both case being transmitted substantially by the air, be it between the web of material 3 and the corrugation tip 8 or be it above the corrugation trough 9. In this case, signal evaluation would be extraordinarily complicated. The inclination of the support 56 by an angle b<90°, which corresponds substantial to the flank angle c, helps attain that, upon passage of the corrugation tip 8, the ultrasonic signal is transmitted substantially through the flank 69, the adhesive bond 12 and the web of material 3 so that, in case of an impeccable adhesive bond 12, a particularly important signal is produced which decreases correspondingly strongly as the web of corrugated board 13 continues to be conveyed.

If there is a defective adhesive bond 12 or if there has been a so-called flank rupture a signal of much lower intensity will result in the place of the expected high-intensity signal. Preliminarily setting certain thresholds will enable this low-intensity signal to be easily converted into a digital signal, with "1" meaning faulty production and "0" no defectivity. FIG. 6 shows the strong potential drop upon passage of two faulty adhesive bonds. Advantages of the device 53 reside in its contactless and inertia-less operation. No important electronic implementation is needed for the simple threshold analysis of the signals of the receiver 63 so that even with very high velocities of the web of material of, for example, 400 min/min, online detection of the adhesive-bond quality is feasible.

Figure 7:
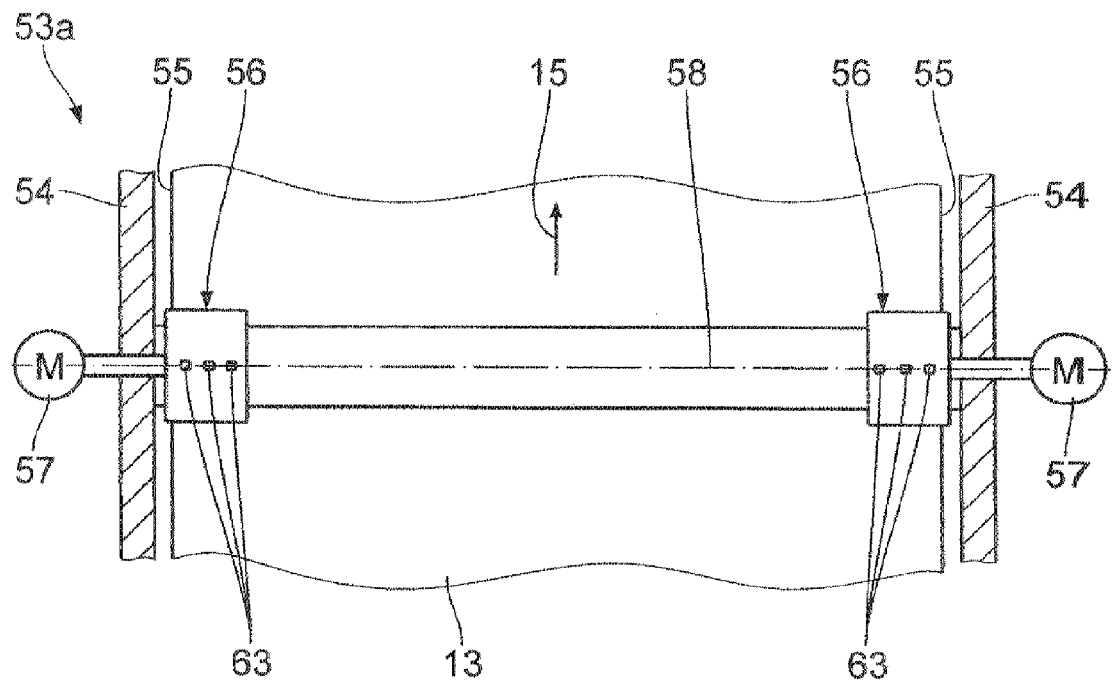
FIG. 7 is an illustration, corresponding to FIG. 3, of a second embodiment.

A second embodiment of the invention will be described below, taken in conjunction with FIG. 7. Constructionally identical parts have the same reference numerals as in the first embodiment, to the description of which reference is made. Constructionally different parts of identical function have the same reference numerals with an a annexed. The essential difference from the first embodiment resides in that several transmitters 62, and several corresponding opposite receivers 63, are disposed side by side on a line. The advantage of this arrangement resides in that the quality of the adhesive bond 12 can be examined over a greater width. Fundamentally it is possible to make the legs 59 and 60 sufficiently long for both supports 56 to enclasp the entire web of corrugated board 13. This is true for all the exemplary embodiments. It is further possible to dispose the transmitters 62 and the associated receivers 63 on a transversal carriage that is displaceable transversely to the working direction 15. In this way it is also possible to check the quality of the adhesive bond 12 over the entire width of the web of corrugated board 13.

Figure 8:
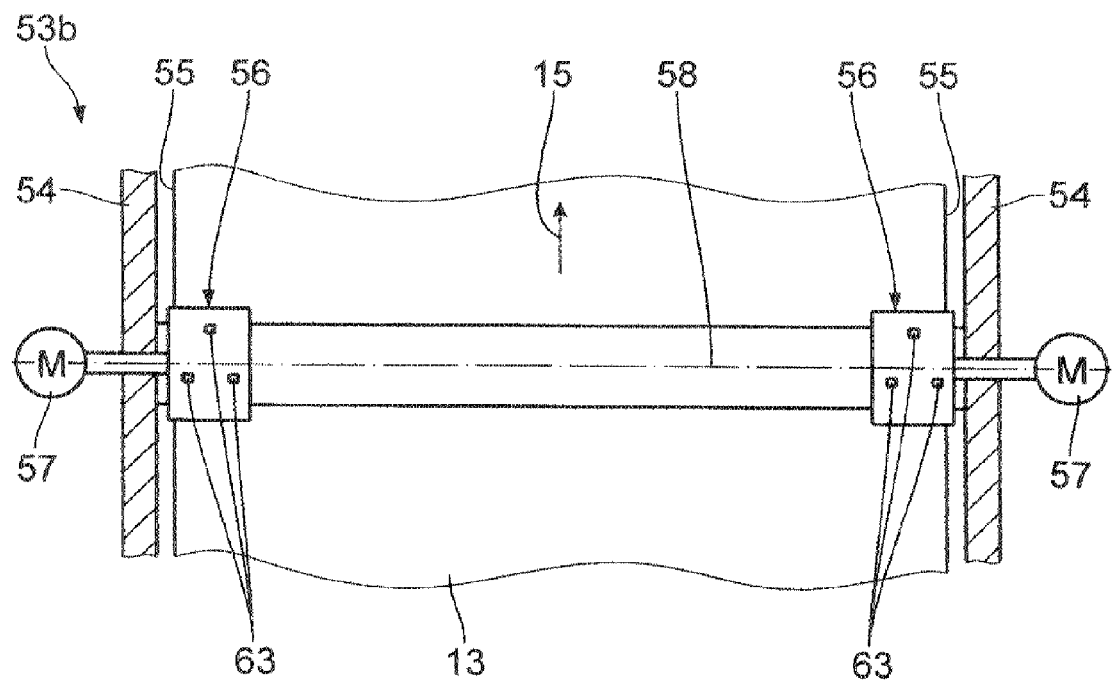
FIG. 8 is an illustration, corresponding to FIG. 3, of a third embodiment.

A third embodiment of the invention will be described below in conjunction with FIG. 8. Identical parts have the same reference numerals as in the first embodiment. Constructionally different parts of identical function have the same reference numerals with a b annexed. The substantial difference from the second embodiment resides in that several transmitters 62 and several associated receivers 63 are provided, which are however not disposed on a line but zigzag. This is accompanied with the advantage that, given a pre-determined length of the legs 59, 60, more transmitters 62 and receivers 63, respectively, can be disposed transversely to the working direction 15 and that those can be arranged more closely. Each transmitter 62 of a predetermined diameter D requires a minimum distance from the adjacent transmitter so that the signals do not overlap on the receiver side. With a given leg length, the arrangement according to FIG. 8 enables more transmitters to be accommodated so that a more accurate analysis of adhesive bonding quality possible.

Figure 9:
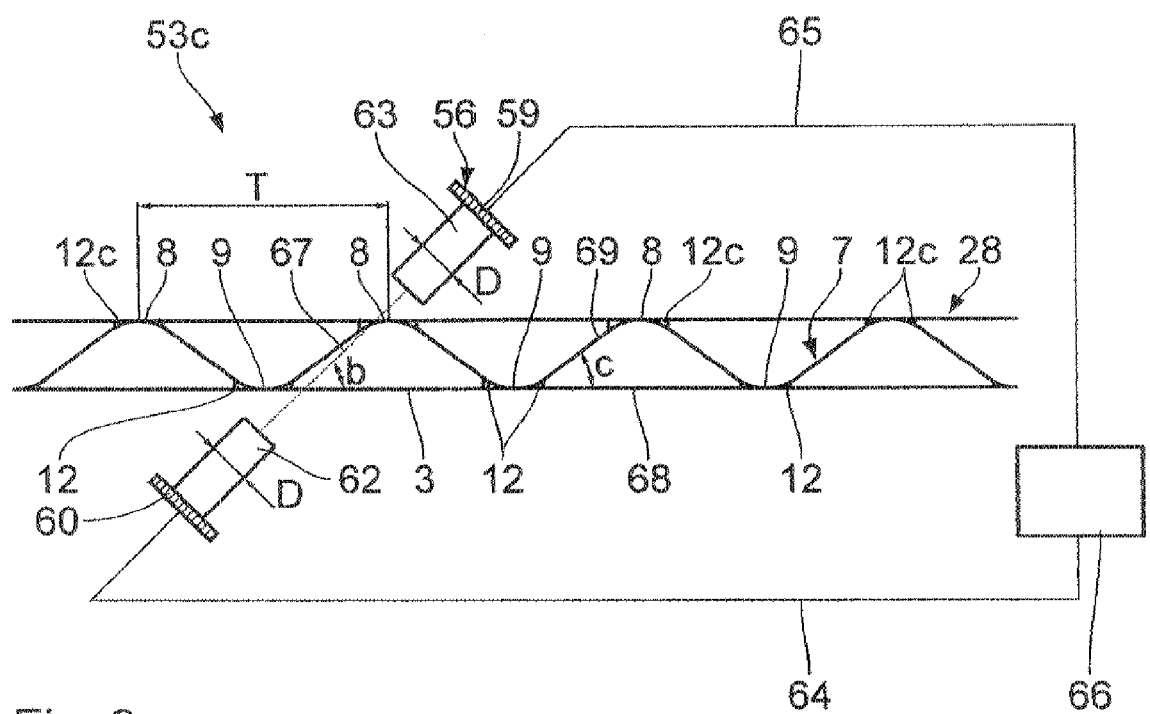
FIG. 9 is an illustration, corresponding to FIG. 5, of a fourth embodiment.

A fourth embodiment of the invention will be described below in conjunction with FIG. 9. Constructionally identical parts have the same reference numerals as in the first embodiment, to the description of which reference is made. Constructionally different parts of identical function have the same reference numerals with a c annexed. The essential difference as compared to the first embodiment resides in that the quality assessment device 53c serves or quality assessment of a web of corrugated board 28 that is composed of three or even more webs of material. Correspondingly, the device 53c is disposed in the working direction 15 downstream of the heater and nip pressure unit 23 and upstream of the cross cutter 37. An arrangement between the longitudinal cutter and scorer unit 29 and the switch 34 is preferred. The device 53c is designed substantially in the same way as the device 53 of the first embodiment. Only the web of corrugated board 28 that is to be examined comprises more webs of material. In this regard, the quality of several adhesive bonds 12, 12c must be examined. Fundamentally, the mode of fault detection is the sane. If adhesive bonds 12, 12c are defective, the transmission of ultrasonic signals is lower there than in ease of perfect adhesive bonding. The device 53c car also be used for examination of webs of corrugated board with further webs of material, for example a web of corrugated board that has three smooth webs of material and two corrugated mediums.

What is claimed is:

1. A machine for the manufacture of a web of corrugated board (13, 28) which is conveyed in a working direction (15), comprising
    at least one smooth liner (3, 19);
    at least one corrugated medium (7) which has corrugation tips (8) and corrugation troughs (9);
    with the corrugated medium (7) and the at least one liner (3) being assembled by adhesion at least in the vicinity of the corrugation troughs (9); and
    a quality assessment device (53; 53a; 53b; 53c) for assessment of the quality of the adhesive bond between the at least one liner (3, 19) and the at least one corrugated medium (7), comprising
        at least one ultrasonic transmitter (62) disposed on one side of the web of corrugated board (13, 28);
        at least one ultrasonic receiver (63) disposed on the opposite side of the web of corrugated board (13, 28) and allocated to the at least one ultrasonic transmitter (62);
        wherein the at least one ultrasonic transmitter (62) and the at least one ultrasonic receiver (63) are located on a straight line (67) which cooperates with the working direction (15) to make an angle (b) to which applies $0°<b<90°$, wherein the corrugated medium (7), between each corrugation tip (8) and each corrugation trough (9), possesses a flank (69) with an angle of slope (c) and that $b \approx c$ applies;
        a control and evaluation unit (66) which, in a manner for data transmission, is connected to the at least one ultrasonic receiver (63) for evaluation of the signal of the ultrasonic receiver (63) and
        wherein the at least one ultrasonic transmitter (62) and the at least one ultrasonic receiver (63) are disposed on a joint support (56) which is pivotable about horizontal pivoting axis (58).

2. A machine according to claim 1, wherein the at least one ultrasonic transmitter (62) and the at least one ultrasonic receiver (63) have the same transversal position as related to the working direction (15) of the web of corrugated board (13, 28).

3. A machine according to claim 1, wherein the corrugated medium (7) has a spacing (T), and by at least one of the ultrasonic transmitter (62) and the ultrasonic receiver (63) has a diameter (D) in the working direction (15), with $D \geq T$ applying.

4. A machine according to claim 1, wherein the at least one ultrasonic transmitter (62) and the at least one ultrasonic receiver (63) are movable transversely to the working direction (15).

5. A machine according to claim 1, wherein at least one of the several ultrasonic transmitters (62) and ultrasonic receivers (63) are disposed transversely to the working direction (15).

6. A machine according to claim 5, wherein at least one of the ultrasonic transmitters (62) and the ultrasonic receivers (63) are disposed on a zigzag line.

7. A machine according to one of the preceding claims, wherein the web of corrugated board (28) comprises a first liner (3), which is applied by adhesion to the corrugated medium (7), and a second liner (19), which is disposed on the other side of the corrugated medium (7) and applied thereto by adhesion.

8. A machine according to claim 1, wherein for the angle (b) applies: $35° \leqq b \leqq 45°$.

* * * * *